US005797402A

United States Patent [19]
West

[11] Patent Number: 5,797,402
[45] Date of Patent: Aug. 25, 1998

[54] DISPOSABLE DRAPE FOR MEDICAL EXAMINATION

[76] Inventor: Raymond O. West, P.O. Box 1137, Belfair, Wash. 98528

[21] Appl. No.: 859,791

[22] Filed: May 19, 1997

Related U.S. Application Data

[63] Continuation of Ser. No. 271,030, Jul. 6, 1994, abandoned.

[51] Int. Cl.$^6$ .................................................. A61B 19/00
[52] U.S. Cl. ........................................ 128/849; 128/850
[58] Field of Search ..................................... 128/849–856

[56] References Cited

U.S. PATENT DOCUMENTS

| | | | |
|---|---|---|---|
| 2,593,121 | 4/1952 | Djorup | 128/849 |
| 3,030,957 | 4/1962 | Melges | 128/856 |
| 3,154,789 | 11/1964 | Lewis | 128/854 |
| 3,494,356 | 2/1970 | Meleges | 128/849 |
| 3,750,664 | 8/1973 | Collins | 128/853 |
| 3,862,632 | 1/1975 | Hinsch | 128/856 |
| 4,041,942 | 8/1977 | Dougan | 128/853 |
| 4,471,769 | 9/1984 | Lockhart | 128/849 |
| 4,903,710 | 2/1990 | Jessamine | 128/849 |
| 4,953,566 | 9/1990 | Garren | 128/849 |
| 5,109,873 | 5/1992 | Marshall | 128/849 |
| 5,140,996 | 8/1992 | Sommers | 128/849 |
| 5,161,544 | 11/1992 | Morris | 128/853 |

*Primary Examiner*—Michael A. Brown
*Attorney, Agent, or Firm*—Christensen, O'Connor Johnson & Kindness PLLC

[57] ABSTRACT

A disposable non-woven drape for use in gynecologic and proctologic examination of female patients. It includes an inexpensive, disposable sheet of non-woven material large enough to provide coverage for the abdomen, perineum and thighs for an adult patient. The distal portion of the drape is incised in such a fashion as to provide sections of the drape. By virtue of gravity, these sections of the drape fall into place and cover the lower abdomen, perineum and thighs, both left and right. This unique invention provides mental comfort, modesty and privacy for the patient and a heightened sense of caring by the physician.

6 Claims, 2 Drawing Sheets

DISPOSABLE DRAPE FOR MEDICAL EXAMINATION

This application is a continuation application of application Ser. Pat. No. 08/271,030, filed on Jul. 6, 1994, now abandoned.

BACKGROUND

1. Field of Invention

1. This invention relates to a disposable non-woven drape for gynecologic and rectal examination by physicians; more specifically this invention provides for a medically related examination that, by its use, is private and discreet. Its major intent is to provide cover of anatomic structures, rather than access to anatomic parts. This fact distinguishes it from the several inventions cited in this application. It utilizes the natural attraction of gravity when employed in its preferred embodiment.

2. Description of Prior Art

2. It is customary in the process of the medically related examination to place a cover over the patient in order to protect one's natural modesty and insure a private, discreet experience. Thereby the patient is readily able to relax and cooperate in the examination process. It is desirable, especially when members of the opposite gender are present in the room, to cover the patient and expose only the portion of the body to be examined.

3. In earlier times, fabric drapes, usually linen, have been employed by physicians for women who, for various reasons, must undergo a gynecologic or rectal examination. In more recent years, because of expense, fabric has been replaced, for the most part by disposable paper drapes.

4. Gynecologic and rectal examinations are common outpatient procedures done by the physician in his/her office. These examinations are necessary for routine papanicolaou smears, to diagnose and to collect specimens for diagnosis of a wide variety of sexually transmitted diseases, to name but a few. Tens of thousands of these examinations are performed daily, throughout the nation.

5. For aesthetic and sanitary reasons, a new drape is employed for each examination. Fabric drapes such as linen are desirable because they have weight and maintain position. They can be folded and molded to provide decorous coverage and consequent modesty; a protection against embarrassing exposure. The disadvantage of fabric drapes is expense. The cost of laundering and pressing is considerable. Consequently they have been largely abandoned in favor of inexpensive disposable drapes manufactured of non-woven material, usually, paper.

6. The advantage of disposable, non-fabric drapes is economy, their cost is remarkably less than reusable, woven drapes. In an era of escalating health-care costs the dollar savings, using non-woven drapes is significant.

7. But plain non-woven drapes have disadvantages too. Because they are light of weight they tend to wander, to become displaced. Further, they resist folding, molding and shaping. In short, they do not provide adequate coverage nor a discreet modest environment for the person who is to be examined. My invention obviates this disadvantage.

8. The drape of U.S. Pat. No. 4,041,942, to Dougan, 1977, embodies a drape to provide means for a sterile field, to avoid contamination. It is intended for use in an operating room as opposed to non-sterile office examinations. It is needlessly cumbersome, redundant, and over-complicated. It provides a slot as means for operating through, whereas my invention, and the sections provided therein are designed as means to afford coverage and modesty. That is, to cover rather than to reveal. Dougan's invention provides for a main sheet as well as a reinforcing sheet. Further, it embodies adhesive binding for edges, and reinforcing tabs. It does not make provision for bridging or perforations as does my invention.

9. The invention in U.S. Pat. No. 2,593121 to Djorup 1950 is a medical examination drape claiming branches and pockets and fastening means, all resulting in a complicated and thus expensive drape. This is inevitable for it was designed for full-body examination rather than simply gynecological and/or rectal examination. It's volume, embodying as it does, full body draping, is far and away redundant, and complicated. Consequently, its cost is virtually prohibitive.

10. My invention is a natural improvement over inexpensive drapes currently extant in tens of thousands of physicians' offices and medical centers. My invention requires no hemming, binding or facing. It needs no pockets for feet and toes. Nor does it require complemental outlet for arms nor fastening means.

11. My invention is simple, effective and importantly, inexpensive.

12. The drape of U.S. Pat. No. 3,494356 to Melges, 1970, Feb. 10, is an obstetrical and surgical drape. It was invented for use in hospital operating suites. While it is disposable, it was invented for sterile operating conditions. For outpatient examinations it is redundant, cumbersome and unnecessarily expensive, in distinct contrast to my invention.

13. The drape of U.S. Pat. No. 4,471,769 to Lockhart, 1984, is a surgical drape, as contrasted with an examination drape. It is designed to provide for a sterile field, rather than for modesty and privacy. My invention does not embody a liquid-impervious sheet, nor an opening for drainage of liquids. Nor does my invention require adhesive tuck forming means. My invention does not embody means for attachment to the surgeon, nor flaps and wings, nor elasticity. All of these add to redundancy, and expense.

14. The drape in U.S. Pat. No. 4,903710 to Jessamine, 1990, Feb. 27, was invented for urologic proctologic and gynecologic surgical procedures. It has elaborate strips, apertures and inspection windows. For simple gynecological and rectal examinations, it is redundant, complicated and unnecessarily expensive in contrast to my invention.

15. The body wrap in U.S. Pat. No. 4,953566 to Garren, 1990, Sep. 4, is a body wrap invented to protect the examiner from contamination during a proctoscopic procedure. When in place, it resembles a diaper with central orifice permitting passage of examining and operative instruments. It is cumbersome, expensive and fails to provide vision and access to female anatomy as necessary for gynecological examination.

OBJECTS AND ADVANTAGES

16. Accordingly, beside the objects, advantages and limitations of drapes described above, several objects and advantages of the present invention are:

a. To provide a disposable medical examination drape that is relatively inexpensive when compared with woven drapes that are reused and require laundering.

b. To provide a disposable drape with sections of the drape that conform to and cover the patient's abdomen, perineal and thigh contours and surfaces.

c. To provide a disposable drape that by virtue of formed sections of the drape and natural forces of gravity stays in place, folded protectively about the patient throughout the examination.

d. To provide a disposable drape that affords, because of its sections, excellent body surface coverage and consequently an enhanced private milieu for the patient's examination.

17. Current plain non-woven drapes lack the ability to maintain station and adequately to cover the patient's abdomen, perineum and thighs. The result is undue exposure of the patient's most private anatomy.

18. In place of the disposable, non-woven drapes currently in wide use, this invention provides a disposable non-woven drape with strategic incisions that form sections of the drape which, in turn, by simple attraction of gravity conform to the patient's body contours covering the heretofore exposed skin surfaces. Thus, my invention overcomes the disadvantages of plain non-woven drapes, currently in wide use. My invention solves a long-felt, long-existing yet unrestricted neck.

19. Further objects and advantages of my invention will become apparent from a consideration of the drawings and ensuing description.

23. REFERENCE NUMERALS IN DRAWINGS

10—Disposable drape
12—Bridge, maintaining drape cohesion
14—Bridge, maintaining drape cohesion
16—Right thigh section of the drape
18—Perineal section of the drape
20—Left thigh section of the drape

SUMMARY

24. My invention is a disposable, non-woven medical drape with incisions that form sections of the drape. These sections of the drape conform to the patient's lower abdomen, perineal and thigh contours. This, in turn, provides privacy for the patient during a medical examination fraught with the potential for embarrassment.

DESCRIPTION OF INVENTION

Figure 1A:
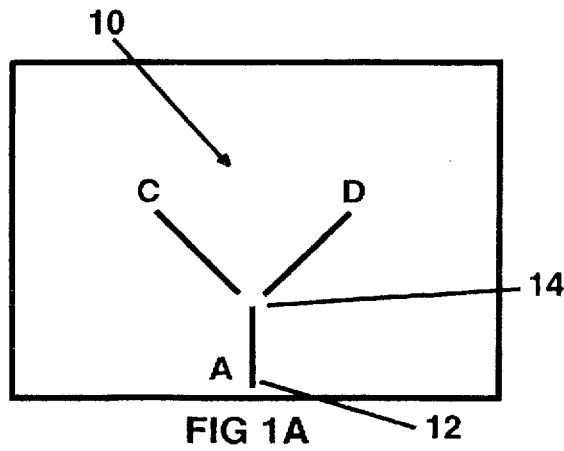
FIG. 1A shows a top view of a non-woven drape of sufficient size to provide discreet coverage for adult patients, with incisions AB, BC & BD.
Figure 1B:
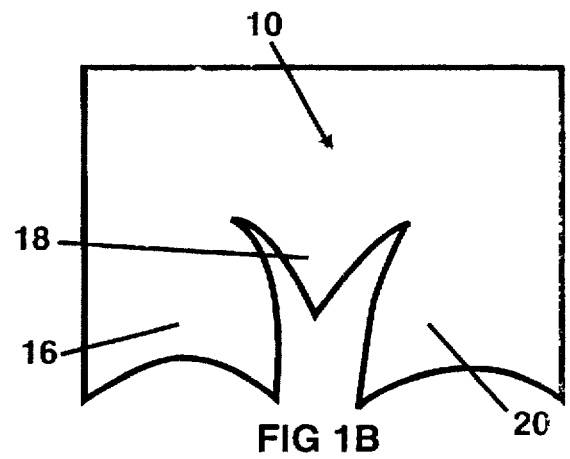
FIG. 1B shows a top view of a non-woven drape 10, in which bridges 12 and 14 have been severed and drape 10 has assumed sections of the drape and curves, as my invention intends, in order to provide patient coverage.
Figure 2B:
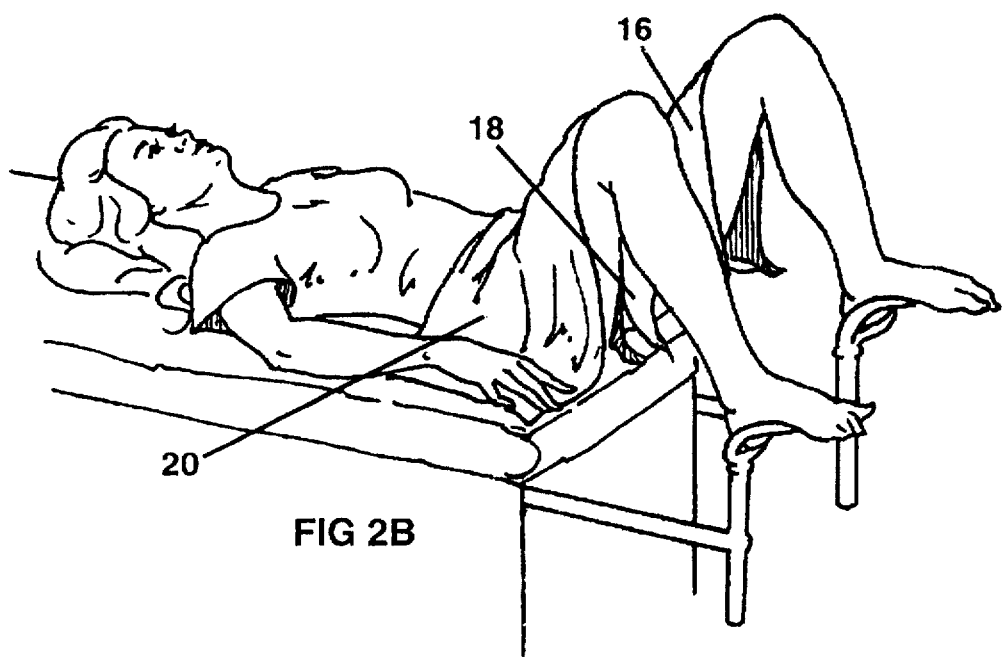
FIGS. 2A, B & C show perspective views of a patient who has assumed the lithotomy position and is draped with a disposable drape as invented by me. Sections 16, 18 and 20 have fallen into place and provide discreet coverage, which in turn enhances modesty.
Figure 2B:
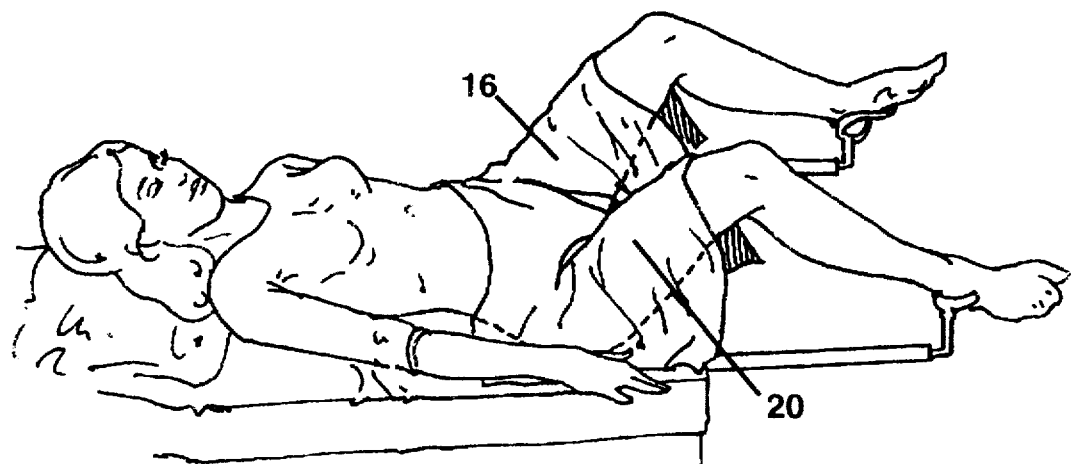
Figure 2C:
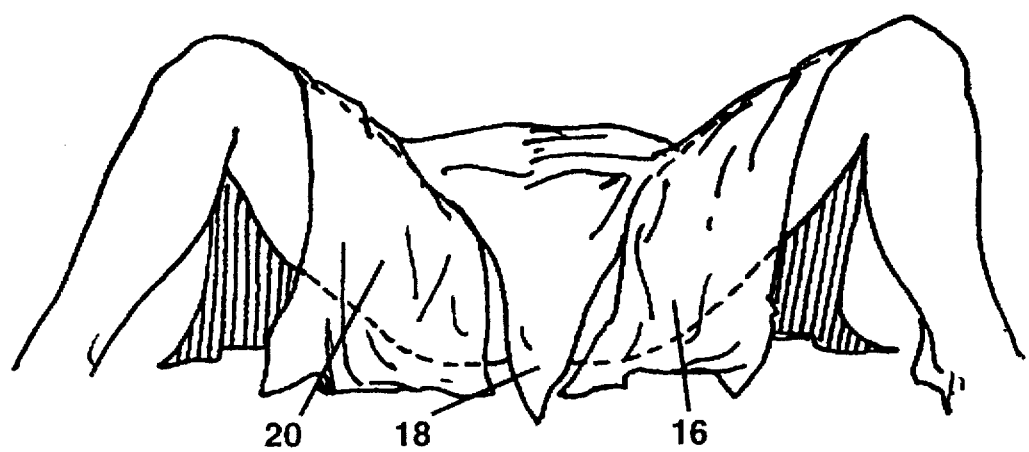

25. Referring more particularly to the drawings, FIG. 1A illustrates drape 10, a non-woven, disposable medical drape with incisions AB, BC & BD. These incisions purposefully incomplete at their ends A&B, resulting in short bridges 12&14. This planned bridging is necessary to maintain stability, ease of handling in drape 10. FIG. 1B specifically shows drape 10 with bridges 12 and 14 severed and sections 16, 18 & 20, in the form that they assume when yielding to natural forces of gravity. Bridges 12 and 14 are easily separated by the examining physician when drape 10 is positioned on the patient. FIG. 2A, B and C illustrate the specific embodiment of the present invention. With the patient lying comfortably on the examining table in lithotomy position the sections 16, 18 & 20 have fallen into place covering the lower abdomen, perineal and thigh surfaces. Referring to FIG. 2A, B & C, it will be noted that drape 10 affords for the patient beneath, a private, discreet milieu for gynecological examination. With further reference to FIG. 2C, it is noted that when the physician is ready to insert vaginal speculum, or complete bimanual examination, she/ he simply repositions section 18, tucking it under the main body of drape 10. This section 18 can be replaced when the examination is completed.

26. If the patient is uncomfortable and moves, tending to displace drape 10, adhesive tabs can be used to temporarily anchor drape 10 to the skin of the medial surface of the thighs.

27. If the patient is unusually large, and if longer incisions are desirable, incisions BC and BD can be lengthened at the time of the examination, thus forming larger sections of the drape.

What is claimed:

1. A medical examination drape comprising:

a nonsterile sheet of nonwoven material sized to cover the central portion of a human body, said nonsterile sheet having a first incision extending inward from the periphery of said nonsterile sheet, said nonsterile sheet having second and third incisions branching from the termination of said first incision, wherein said first, second, and third incisions collectively form a "Y" shape.

2. The medical examination drape of claim 1, wherein said drape is formed from a disposable material.

3. The medical examination drape of claim 1, wherein said drape is opaque.

4. The medical examination drape of claim 1, wherein said drape is of rectangular shape and said first incision is made orthogonally to a side of said drape.

5. The medical examination drape of claim 1, wherein said incisions allow said medical drape to utilize the natural attraction of gravity on said drape so as to conform to the curves and surfaces of the lower abdomen, vulva, perineum, and thighs.

6. The medical examination drape of claim 1, further including adhesive tabs for stabilizing said drape to said human body.

* * * * *